United States Patent [19]

Cobia et al.

[11] Patent Number: Plant 7,173

[45] Date of Patent: Feb. 27, 1990

[54] PLANT OF THE CACTACEAE PLANT FAMILY

[75] Inventors: Barnell L. Cobia, Winter Garden; Mark E. Cobia, Orlando, both of Fla.

[73] Assignee: B. L. Cobia, Inc., Winter Garden, Fla.

[21] Appl. No.: 282,315

[22] Filed: Dec. 9, 1988

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Roger L. Martin

[57] ABSTRACT

A new and distinct plant variety of the Cactaceae family is of the type known commercially as a "Christmas Cactus" and has a growth habit similar to that of the "Gold Charm" variety but has buds and sterile flowers with somewhat different color characteristics from those of the "Gold Charm" variety.

4 Drawing Sheets

BACKGROUND OF THE INVENTION

The invention relates to a new and distinct plant variety of the Cactaceae family and which has been named the *Zygocactus truncatus* 'Christmas Flame' by the inventor.

Certain plant varieties of the Cactaceae family are well known in the foliage plant market and among these are those which are commonly referred to as the Christmas Cactus varieties because they tend to bloom during the Thanksgiving–Christmas holiday season.

The Christmas Cactus varieties on the market have blooms which vary in color from one variety to the next as is evident from the current U.S. patent art. However, the only Christmas Cactus variety known to the inventors and which has a generally "yellow" colored bloom is the "Gold Charm" variety which forms the subject matter of U.S. Plant Pat. No. 5,104.

A general objective has been to develop a new plant variety which is distinguishable from the "Gold Charm" variety and which is capable of being marketed competitively therewith.

SUMMARY OF THE INVENTION

The new plant variety was developed in a nursery located at Winter Garden, Fla., from a natural mutation that appeared on a specimen of the "Gold Charm" variety which was under cultivation at the nursery.

Through successive propagations of cuttings taken from the mutated plant part, it has been ascertained that specimens of the new plant variety generally resemble the "Gold Charm" variety in most respects but are distinguishable from this variety and from other related varieties known to the inventors by a growth habit which is evident in plant specimens of the new variety which have been propagated and grown under nursery conditions utilized in the growing of tropical plants in Winter Garden, Fla., as combining the following principal characteristics:

1. An erect growth habit,

2. Buds with (a) an ovary having a basic field during immaturity in which the color is usually dominated by a red hue, and in which, with further maturity of the bud, there is a development of random areas in which the color is dominated by a yellow green hue, and (b) petals having a basic field during bud immaturity in which the color is usually dominated by a red and/or pink hue and in which, with further maturity of the bud, there is a development of streaks in which the color is dominated by a yellow green and/or olive green hue, and 3. Sterile flowers having tepals with (a) a narrow marginal blade area that in color is dominated by a reddish orange, orange, orange yellow and/or pink hue, and (b) a center blade area that in color is dominated by a yellow hue and merges distally with the color in the basal area of the tepal blade.

BRIEF DESCRIPTION OF THE DRAWINGS

The accompanying drawings serve by color photographic means to illustrate the new plant variety and wherein one sheet shows a ten (10) month old specimen which was grown from the propagation of a single phylloclade in a conventional 3" pot found in the marketplace. A second sheet shows an enlargement of a fully open bloom taken from the specimen shown in the photograph of the previously mentioned sheet. Still another sheet shows a bloom as sectioned generally longitudinally through the perianth tube and ovary to expose the style and stamen arrangement. The last sheet shows two horizontal rows of phylloclades that bear buds in various stages of development, the phylloclades in the bottom row having been taken from specimens of the new plant variety while the phylloclades in the top row were taken from a specimen of the "Gold Charm" variety and are shown to provide comparison.

DETAILED PLANT DESCRIPTION

The following is a detailed description of the new plant variety with colors and hues, unless otherwise clearly indicated by the text as, for example, through the absence of color notations, being named in accord with the ISCC-NBS Method of Designating Colors (U.S. Dept. of Commerce, National Bureau of Standards, Circular 553), the named colors being interpreted from color notations derived by comparison with the color specimens of the Munsell Book of Color. The description is further based on observations of well fertilized plants of about one year of age from initial propagation which were grown under 50–75% shaded glasshouse nursery conditions in the Winter Garden, Fla. area and wherein temperatures range from 60°–85° F. during the winter months, from 75°–95° F. during the summer months, and are ambient during the intervening periods.

I. Name: *Zygocactus truncatus* 'Christmas Flame'.

II. Parentage: This variety was developed from a natural mutation that occurred on a specimen of the variety known as *Zygocactus truncatus* 'Gold Charm' (See U.S. Plant Pat. No. 5,104).

III. Classification:

A. *Botanic* (*Britton and Rose, The Cactaceae,* Constable and Co., Ltd., London 1937, Vol. IV).—(1) Family: Cactaceae. (2) Tribe: Cereeae. (3) Sub-Tribe: Epiphyllanae. (4) Genus: Zygocactus. (5) Species: *Truncatus* (Haworth) Schumann.

B. *Commercial.*—Thanksgiving-Christmas blooming cactus.

IV. Form: Epiphylic and terrestrial shade loving, succulent, leafless plant with jointed and branched stems.

V. Stems:

A. *General.*—Irregular with usually multichotomous branching of both upright and pendulous, adventitiously rootable, flattened phylloclades that have a prominent midrib and prominently toothed lateral wings.

B. *Phylloclades.*—(1) General: Elongated and flat with a transversely elongated, areole bearing, truncated apex, with inwardly tapering basal wing margins that merge with a usually broadly pointed basal juncture with the phylloclade therebelow, and with an axially located areole usually being associated with each tooth. (2) Midrib: (a) General — Extends longitudinally of phylloclade and continuously through joints and with a laterally tapering cortex at the wing insertions. Pith surrounding vascular bundles that branch and provide lateral extensions of the vascular system to the marginal teeth. (b) Texture — Smooth, waxy epidermis with wax in small embedded scales and becoming woody in basal stem areas with specimen aging. (c) Size (at maturity) — 1. Length: Usually 38–66 mm. 2. Thickness: Usually 2.5–6 mm. (d) Color (at maturity) — Usually dominated by a yellow green and/or olive green hue and commonly moderate yellow green (7.5 GY 5/6) and/or moderate olive green (7.5 GY 3/4) (7.5 GY 4/4) (7.5 GY 4/6). (3) Wings: (a) General — Dentate and generally flattened from midrib cortex to tooth insertions and with slight thinning taper toward margins. (b) Margins — Toothed. (c) Texture — Succulent to leathery with smooth, waxy epidermis where the wax is arranged in small embedded scales of higher density than in midrib area, and becoming corky in the basal stem areas with specimen aging. (d) Size (at maturity) — 1. Thickness: About 1–3 mm in the area intermediate the margin and midrib. 2. Width: Usually 15–28 mm as measured from phylloclade axis to most offset lateral areole. 3. Color (at maturity) — Usually dominated by a yellow green and/or olive green hue and commonly moderate yellow green (7.5 GY 5/6) and/or moderate olive green (7.5 GY 3/4) (7.5 GY 4/4) (7.5 GY 4/6). (4) Teeth: (a) Shape — 1. General: Generally flattened and tapered along the margins and from the wing insertion to an apex having a hyaline, single cell, pointed spine with nonpredictable bending. 2. Abaxial margin: Usually straight to convex. 3. Adaxial margin: Usually straight to concave. (b) Orientation — Generally project distally of phylloclade in an alternate arrangement at an angle in the range of 10°–40° with the midrib and usually at an angle in the range of 20°–30° with the midrib. (c) Margins — Entire. (d) Texture — Succulent to leathery with smooth waxy epidermis having wax in small embedded scales of density comparable to wings, and becoming corky in basal stem areas with specimen aging. (e) Size (at maturity) — 1. Thickness: Usually 0.5–2 mm in center area. 2. Areole to apex dimension (adaxial marginal side): Usually 4–15 mm in the upper quadrants of the phylloclades. (f) Number — Usually 5–9 per phylloclade. (g) Color — Usually dominated by a yellow green and/or olive green hue and commonly moderate yellow green (7.5 GY 5/6) and/or moderate olive green (7.5 GY 3/4) (7.5 GY 4/4) (7.5 GY 4/6). (5) Areoles: (a) Terminal areole — Large, elongated, oval shaped with several acicular bristles, and several buds that may mature into either new phylloclades or flowers. The opposite ends of the areole are located adjacent to subsidiary areoles which are in turn located at the axils of the teeth at the distal end of the phylloclade. (b) Axillary areoles — Acicular bristles without glochidia but having copious, short, brownish, multicellular, wooly hairs. In areoles located below the teeth at the distal end of the phylloclade, there is usually only one areole which is frequently latent.

VI. Buds:

A. *General.*—Unarmored, ovoid and chlorophyllous.

B. *Color* (*when bud length, including ovary and pedal is* 8–15 *mm*).—1. Ovary: A basic field during bud immaturity in which the color is usually dominated by a red hue, and in which, with further maturity of the bud, there is a development of random areas in which the color is dominated by a yellow green hue. Commonly, dark red (2.5 R 3/6) (2.5 R 3/4) and/or moderate red (2.5 R 4/8) in the basic field and moderate yellow green (2.5 GY 6/6) (2.5 GY 7/6) in the randomly developed areas. 2. Petals: A basic field during bud immaturity in which the color is usually dominated by a red and/or pink hue and in which, with further maturity of the bud as the petals develop and become exposed, there is a development of streaks which in color are dominated by a yellow green and/or olive green hue. A basic field which is commonly moderate red (2.5 R 5/10) (2.5 R 5/8) (2.5 R 4/8), grayish red (2.5 R 4/6) and/or deep pink (2.5 R 6/10) (2.5 R 6/8) and streaks which are commonly moderate yellow green (5 GY 5/6), moderate olive green (5 GY 4/4) and/or strong yellow green (5 GY 6/8).

VII. Flowers:

A. *General.*—Sessile, zygomorphic, usually solitary, terminal, perfect and epigynous with double hypanthium and whorled tepals (undifferentiated sepals and petals) having a spiral emergence as a perianth provided with a sepaloid series of free tepals, a tube laminating series of tepals, and a tube forming series of united tepals.

B. *Sepaloid series.*—(1) General: Free tepals inserted on top of ovary. (2) Shape: Deltoid in outer members of whorl and grading inwardly in the whorl to provide progressively greater length dimensions and broader apices. All members have a pointed tip and entire margins with sparse irregular teeth appearing mainly in the apex areas of the inner members of the whorl. (3) Texture: Succulent and glabrous outer whorl members and grading inwardly in whorl to silken blades with fleshy basal areas. (4) Number: Usually 5–6. (5) Size (at full bloom): (a) Length (base-tip dimension) — Usually less than 17 mm. (b) Width (maximum) — Usually less than 12 mm. (6) Color (at full bloom): Varies from the outer members to the inner members with the smallest outer whorl tepals usually having a continuous field that in color is dominated by a yellow green hue. The inner whorl tepal members have a narrow marginal blade area that in color is dominated by a reddish orange and/or pink hue, and a center blade area which in color is dominated by a yellow hue and merges proximally with a translucent white in the basal area. Commonly moderate reddish orange (10 R 6/10) (10 R 5/10), deep pink (2.5 R 6/10), and/or strong pink (2.5 R 7/8) in the marginal blade areas of the inner whorl tepal members. Commonly light yellow (2.5 Y 9/6) in the center blade areas and merging proximally with white (2.5 GY 9/0) in the basal areas of the inner whorl members. Commonly strong yellow green (2.5 GY 7/8) (2.5 GY 6/8) (5 GY 7/10) and/or brilliant yellow green (5 GY 8/8) in the outer whorl members. (7) Orientation: Erect to recurve at full bloom.

C. *Tube laminating series.*—(1) General: Tepals inserted on ovary and basally united below the throat as outer laminations on the perianth tube and with progressively greater amount of basal fusion inwardly in the whorl. (2) Shape: Zygomorphic and grading inwardly in the whorl with progressively greater length dimensions and broader apices so that the blade area changes inwardly in the whorl from ovate with an acute tip to spatulate with a broader acute tip. Entire margins with sparse, irregular teeth mainly in apex areas. (3) Texture: Succulent and glabrous outer whorl members and grading inwardly to silken blades with slightly fleshy basal areas. (4) Number: Usually 7–11 tepals. (5) Size (at full bloom): (a) Length (base-tip dimension) — Usually ranging from about 15 to about 64 mm. (b) Width (maximum) — Usually ranging from about 10 to about 19 mm. (6) Color (at full bloom): (a) General — Tepals with a basal area that is translucent white immediately above the insertion, has a narrow marginal area that in color is dominated by a reddish orange, orange and/or an orange yellow hue, and with a center blade area that in color is dominated by a yellow hue and merges proximally with the color in the basal area of the tepal. (b) Basal area — Translucent white at insertion and along tube attached area. Commonly white (2.5 RP 9.5/0). (c) Blade area — Commonly moderate reddish orange (10 R 6/10) (10 R 5/10), moderate orange (near 2.5 YR 7/10) strong orange (near 2.5 YR 7/10) and/or moderate orange yellow (10 YR 7/8) in the marginal blade areas. Commonly light yellow (2.5 Y 9/6) (near 2.5 Y 8/8), moderate yellow (near 2.5 Y 8/8), strong yellow (near 2.5 Y 8/10) (near 2.5 Y 8/8), and/or brilliant yellow (near 2.5 Y 8/10) (near 2.5 Y 8/8) in the center blade areas. (7) Orientation: Perpendicular to recurve at full bloom.

D. *Tube forming series.*—(1) General: Tepals basally united to form hollow perianth tube that is inserted on ovary and equipped at its throat with an irregular carina (keel). (2) Shape: (a) Perianth tube — Elongated and elipsoidal in cross section with the major ellipsoidal axis usually generally normal to the plane of the supporting phylloclade. (b) Blades — Nearly zygomorphic and thinly spatulate with acute tips and entire margins having sparse irregular teeth in apex area. (c) Carina (keel) — Irregular and transcending. (3) Texture: (a) Perianth tube — Thick, succulent and slightly ribbed. (b) Blades — Translucent and silken. (c) Carina (keel) — Fleshy. (4) Number: Usually 8–9. (5) Size (at full bloom): (a) Perianth tube — 1. Length (base-keel): Usually 32–40 mm along tube axis. 2. Major Axis: Usually 13–16 mm at throat interior. 3. Minor axis: Usually 7–10 mm at throat interior. (b) Blades — 1. Length (keel-tip): Usually 22–37 mm. 2. Width (maximum): Usually 10–16 mm. (6) Color (at full bloom): (a) Perianth Tube — A basic field that is translucent white with longitudinally extending, randomly arranged striations or streaks that in color are purplish white and/or dominated by a purplish pink hue. Commonly a white (2.5 RP 9.5/0) basic field with striations and/or streaks that are purplish white (5 RP 9/1) and/or pale purplish pink (5 RP 9/2). (b) Blades — Distally of the keel there is a narrow marginal blade area that in color is dominated by an orange yellow hue, and a center blade area that in color is dominated by a yellow hue and merges proximally with a white and/or color dominated by a purplish pink hue in the basal area distally of the keel. Commonly light orange yellow (near 10 YR 8/8), moderate orange yellow (near 7.5 YR 7/10) (near 10 YR 8/8) and/or strong orange yellow (near 7.5 YR 7/10) in marginal blade areas. Commonly light yellow (2.5 Y 9/6), strong yellow (near 2.5 Y 8/10), brilliant yellow (near 2.5 Y 8/10) and/or vivid yellow (2.5 Y 8/12) in the center blade areas of the blade. Commonly white, purplish white (5 RP 9/1) and/or color dominated by pale purplish pink (5 RP 9/2) in the basal area distally of the keel. (c) Carina (keel) — Color usually dominated by a purplish pink and/or purplish red hue. Commonly deep purplish pink (5 RP 6/10) and/or moderate purplish red (5 RP 5/10). (7) Orientation: Acute to recurve.

E. *Androecium* (*stamens*).—(1) General: Numerous exserted and diadelphous stamens with one group having filaments basally fused to the perianth tube and the other group having filaments basally united to form a nectary housing, thin annulus around the style and which is provided with thin, deflexed, irregular, toothed margin or ruffle at the throat of the annulus. (2) Stamen number: (a) Tube attached group — Usually 83–101. (b) Basally united group — Usually 19–24. (3) Filaments: (a) General — Translucent with anther connective. (b) Shape — Long, slender, terete. (c) Texture — Glabrous and capillaceous. (d) Color — Translucent white over entire length. (e) Size (at full bloom) — 1. Length: a. Tube attached group — Usually 41–65 mm. b. Basally united group — Usually 33–51 mm. 2. Diameter: Usually about 0.4 mm intermediate opposite ends. (4) Anthers: (a) General — Adnate with four longitudinally dehiscent pollen sacs and connective inserted at end. (b) Shape — Elongated. (c) Texture — Waxy. (d) Color (before dehiscence) — Dominated by a yellow hue. Commonly light yellow (5 Y 9/6). (e) Sterility — Sterile.

F. *Gynoecium* (*pistil*).—(1) General: Exserted with compound, pariental placentation and united style surrounded by annular diffuse yellowish nectary at its insertion. (2) Style: (a) General — Hollow, stout and inserted at ovary. (b) Shape — Elongated and terete. (c) Texture — Fleshy and smooth. (d) Color — Usually dominated by a reddish purple, and/or purplish red hue in the proximal area, by a reddish purple in the distal area and by a reddish purple and/or red hue in the center areas that merges proximally and distally with the colors in the proximal and distal areas. Commonly moderate purplish red (5 RP 5/10), and/or strong reddish purple (2.5 RP 5/10) (2.5 RP 4/10) in the basal areas. Commonly strong reddish purple (2.5 RP 5/10), strong red (5R 5/12) and/or vivid red (5 R 4/14) in the center areas. Commonly strong reddish purple (2.5 RP 5/10) (2.5 RP 4/10) in the distal areas. (e) size (at full bloom) — 1. Length: Usually 40–62 mm. 2. Diameter: Usually 0.5–1.0 mm intermediate opposite ends. (3) Stigma: (a) General — Exserted and erect with usually 6–7 inner marginally adhering lobes. (b) Shape — Elongated and tapering toward lobe tips and having relatively blunt apices. (c) Texture — Fleshy and smooth with inner sides of lobes having short glutinous capillaceous hairs. (d) Color — Usually dominated by a purplish pink hue. Commonly light purplish pink (5 RP 8/6) and/or moderate purplish pink (5 RP 7/8). (e) Size — 1. Length: Usually 3–5 mm along inner margins. (4) Ovary: (a) General — Inferior with thin epidermis and usually 6–8 carpules with numerous ovules. (b) Shape — Terete to ovoid and generally broadening from insertion to floral end. Ribbed single concavity with inserted style. (c) Texture — Succulent with glabrous thin outer epidermis. (d) Color — A basic field with color usually dominated by a red hue and provided with random areas which, in color, are dominated by a yellow green hue. Commonly grayish red (2.5 R 4/6) and/or moderate red (2.5 R 4/8) in the basic field and with moderate yellow green (2.5 GY 6/6) (2.5 GY 7/6) in the random areas. (e) Size — 1. Length: Usually 8–10 mm from insertion to cavity base. 2. Major axis: Usually 9–10 mm at distal end of concavity. 3. Minor axis: Usually about 7–9 mm at distal end of concavity.

VIII. Growth habit: Erect.

General Description of a Plant Specimen

Age of plant: Ten (10) months from initial propagation of single phylloclade.

Branches from propagated phylloclade: Three (3).

Total number of new phylloclades grown: Sixteen (16).

GENERAL:

| Branch No. | No. of Phylloclades | Maximum Branch Length | No. of Tips |
|---|---|---|---|
| 1 | 5 | 169 mm | 2 |
| 2 | 6 | 167 mm | 3 |
| 3 | 5 | 161 mm | 3 |

MIDRIBS:

| Branch No. | Average Midrib Length | Average Midrib Thickness |
|---|---|---|
| 1 | 56.4 mm | 3.8 mm |
| 2 | 52.3 mm | 3.8 mm |
| 3 | 53.6 mm | 3.4 mm |

WINGS:

| Branch No. | Average Wing Center Thickness | Average Wing Width (Maximum) |
|---|---|---|
| 1 | 2.1 mm | 21.2 mm |
| 2 | 2.3 mm | 19.7 mm |
| 3 | 2.2 mm | 18.2 mm |

TEETH:

| Branch No. | Teeth (Avg.) per Phylloclade | Average Tooth Center Thickness | Average Aerole To Apex Length |
|---|---|---|---|
| 1 | 7.2 | 1 mm | 6.9 mm |
| 2 | 7.4 | 1 mm | 7.4 mm |
| 3 | 7.0 | 1 mm | 7.2 mm |

Phylloclade color: Moderate yellow green (7.5 GY 5/6) and moderate olive green (7.5 GY 3/4) (7.5 GY 4/4) (7.5 GY 4/6).

General Description of a Flower

The following is a general description of a flower of the new plant variety and which bloomed in December on a 10 month old plant specimen grown under shaded greenhouse nursery conditions in Winter Garden, Fla.

No. of buds and blooms on plant specimen: 22.

Bloom life: 7–9 days.

Sepaloid series of tepals:

*Number.*—5.

*Tepal size* (*at full bloom*).—Maximum base-tip dimension: 15 mm. Minimum base-tip dimension: 3 mm. Maximum width dimension: 11 mm.

*Color* (*at full bloom*).—Strong yellow green (2.5 GY 7/8) (2.5 GY 6/8) (5 GY 7/10) in the continuous fields of the outer whorl members. Moderate reddish orange (10 R 6/10) and strong pink (2.5 R 7/8) in the marginal areas of the inner whorl members and light yellow (2.5 Y 9/6) in the center field areas of the inner whorl members. Strong yellow green (2.5 GY 7/8) (2.5 GY 6/8) (5 GY 7/10) and brilliant yellow green (5 GY 8/8) in the basal areas of the inner whorl members.

Tube laminating series of tepals:

*Number.*—10.

*Size* (*at full bloom*).—Maximum base-tip dimension: 62 mm. Minimum base-tip dimension: 16 mm. Maximum blade width: 18 mm. Minimum blade width: 10 mm.

*Color.*—Moderate reddish orange (10 R 6/10) (10 R 5/10), moderate orange yellow (10 YR 7/8), moderate orange (near 2.5 YR 7/10), strong orange (near 2.5 YR 7/10), brilliant yellow (near 2.5 Y 8/10), strong yellow (near 2.5 Y 8/10) and light yellow (2.5 Y 9/6) in the center field areas of the blades and translucent white in the basal areas of the blades.

Tube forming series of tepals:

*Number.*—9.

*Size (at full bloom).*—Periant tube: Length (base to keel) — 39 mm along tube axis. Major axis — 14 mm at throat interior. Minor axis — 9 mm at throat interior. Blades: Maximum length (keel-tip) — 34 mm. Minimum length (keel-tip) — 30 mm. Maximum blade width — 15 mm. Minimum blade width — 12 mm.

*Color.*—Perianth tube: A basic field that is generally translucent and white (2.5 RP 9.5/0) with random striations of pale purplish pink (5 RP 9/2). Blades: White (2.5 RP 9.5/0), purplish white (5 RP 9/1) in basal areas distally of the keel. Strong orange yellow (near 7.5 YR 7/10) and moderate orange yellow (near 7.5 YR 7/10) in marginal areas of blades, and vivid yellow (2.5 Y 8/12), brilliant yellow (near 2.5 Y 8/10) and strong yellow (near 2.5 Y 8/10) in the center field area.

Androecium:

*Stamen number.*—Tube attached group: 98. Basally united group: 20.

*Filaments.*—Color: translucent white.

*Size (at full bloom).*—Length — Tube attached group: 58 mm (avg). Basally united group: 42 mm (avg). Diameter: About 0.40 mm intermediate the opposited ends.

*Anthers.*—Color (before dehiscing): Light Yellow (5 Y 9/6).

Gynoecium (pistil):

*Style.*—Color: Moderate purplish red (5 RP 5/10) and strong reddish purple (2.5 RP 5/10) in basal area and strong reddish purple (near 2.5 RP 5/10) (2.5 RP 4/10) in distil area. Size (at full bloom): Length — 59 mm. Diameter — 1 mm intermediate opposite ends.

*Stigma.*—Color: Moderate purplish pink (5 RP 7/8) and light purplish pink (5 RP 8/6). Size: 4 mm (avg) lobe length.

*Ovary.*—Color: Moderate yellow green (near 2.5 GY 6/6) (2.5 GY 7/6) and grayish red (2.5 R 4/6). Size (at full bloom): Length (insertion to concavity base) — 10 mm. Major axis — 10 mm at distal end of concavity. Minor axis — 8 mm at distal end of concavity.

We claim:

1. A new and distinct plant variety of the Cactaceae family as shown and described and which is mainly distinguished from its antecedents and known related varieties by a growth habit which is substantially like that of the "Gold Charm" variety but as modified by the combination of the following characteristics:

(1) An erect growth habit, (2) Buds with (a) an ovary having a basic field during immaturity in which the color is usually dominated by a red hue, and in which, with further maturity of the bud, there is a development of random areas in which the color is dominated by a yellow green hue, and (b) petals having a basic field during bud immaturity in which the color is usually dominated by a red and/or pink hue and in which, with further maturity of the bud, there is a development of streaks in which the color is dominated by a yellow green and/or olive green hue, and (3) Sterile flowers having tepals with (a) a narrow marginal blade area that in color is dominated by a reddish orange, orange, orange yellow and/or pink hue, and (b) a center blade area that in color is dominated by a yellow hue and merges distally with the color in the basal area of the tepal blade.

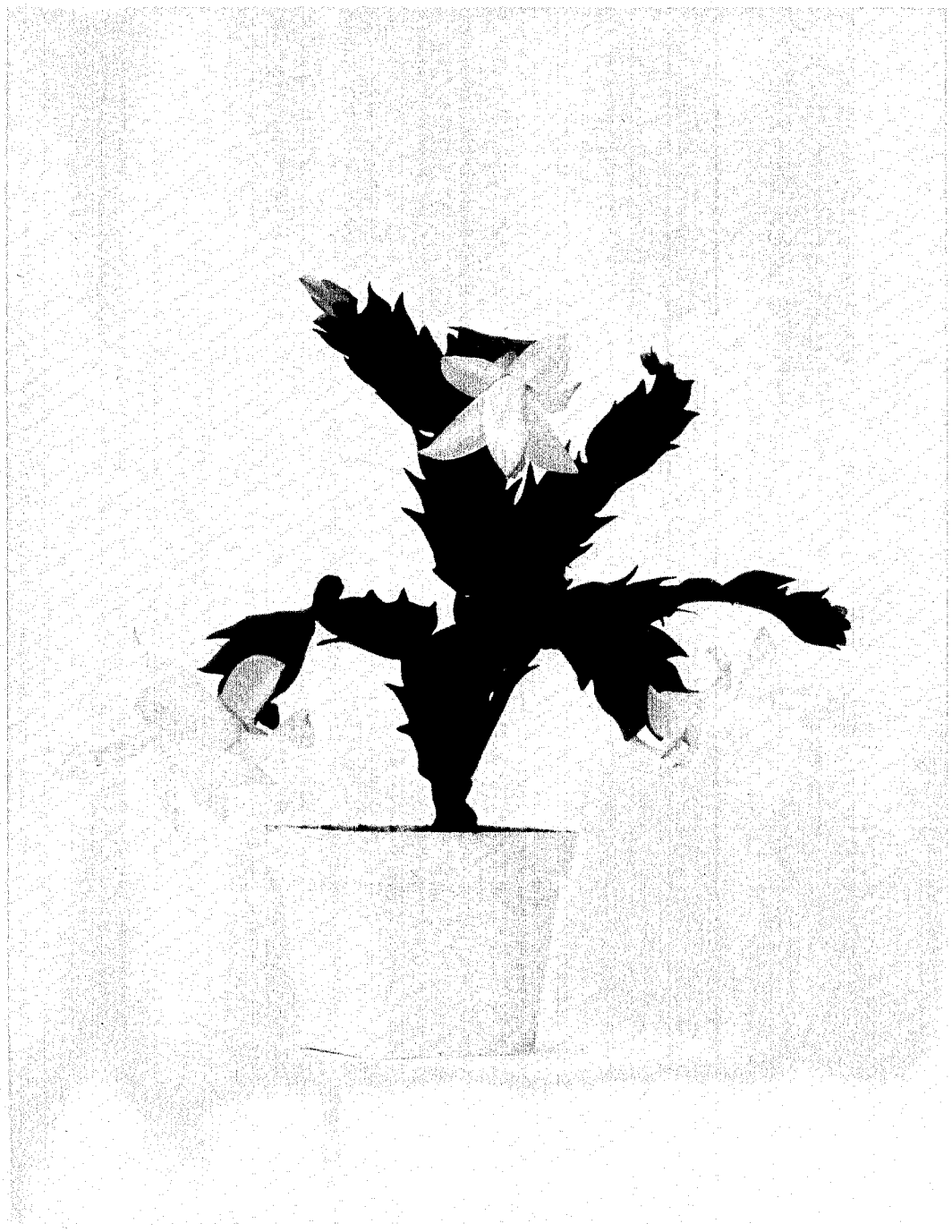

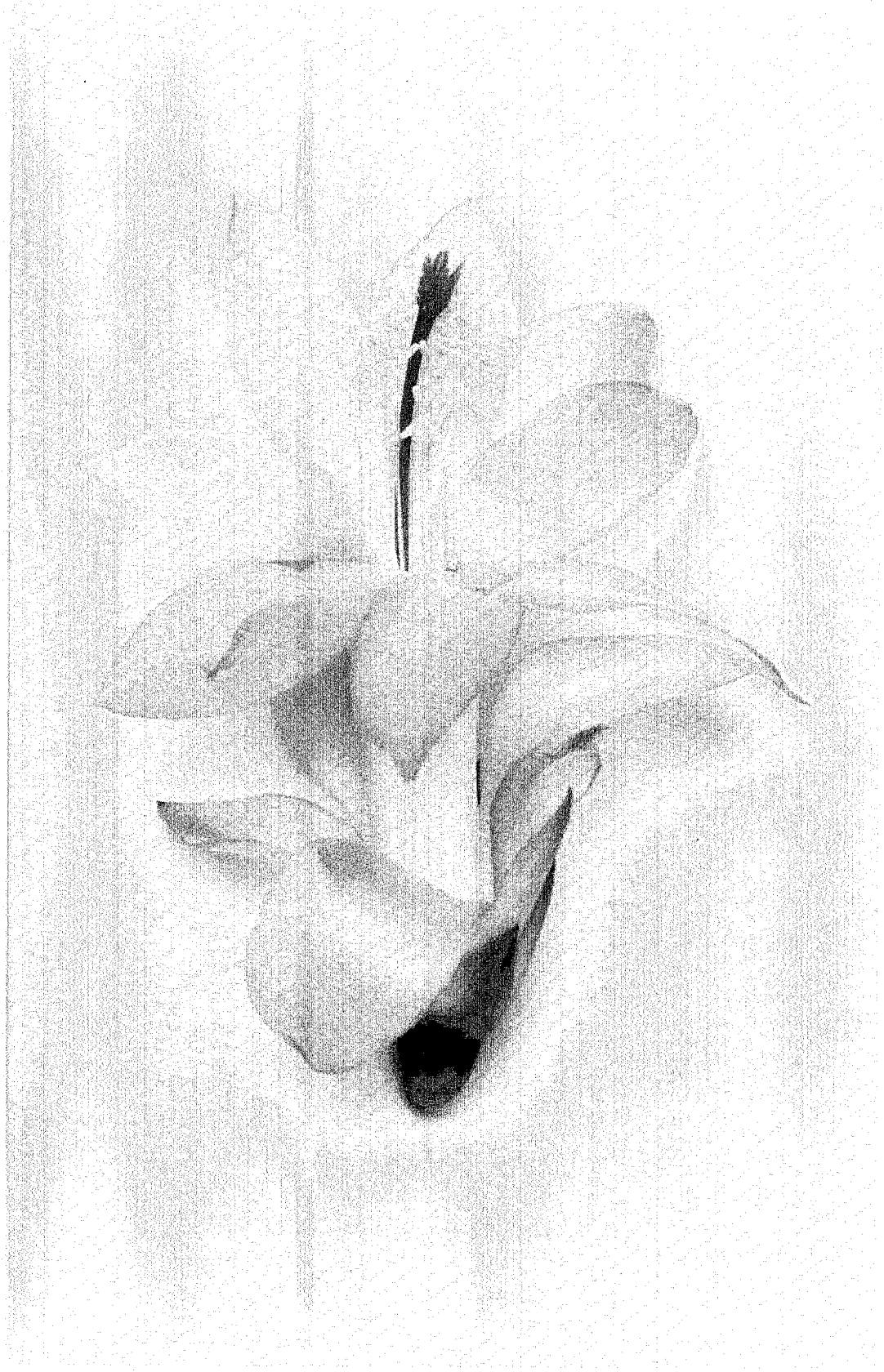

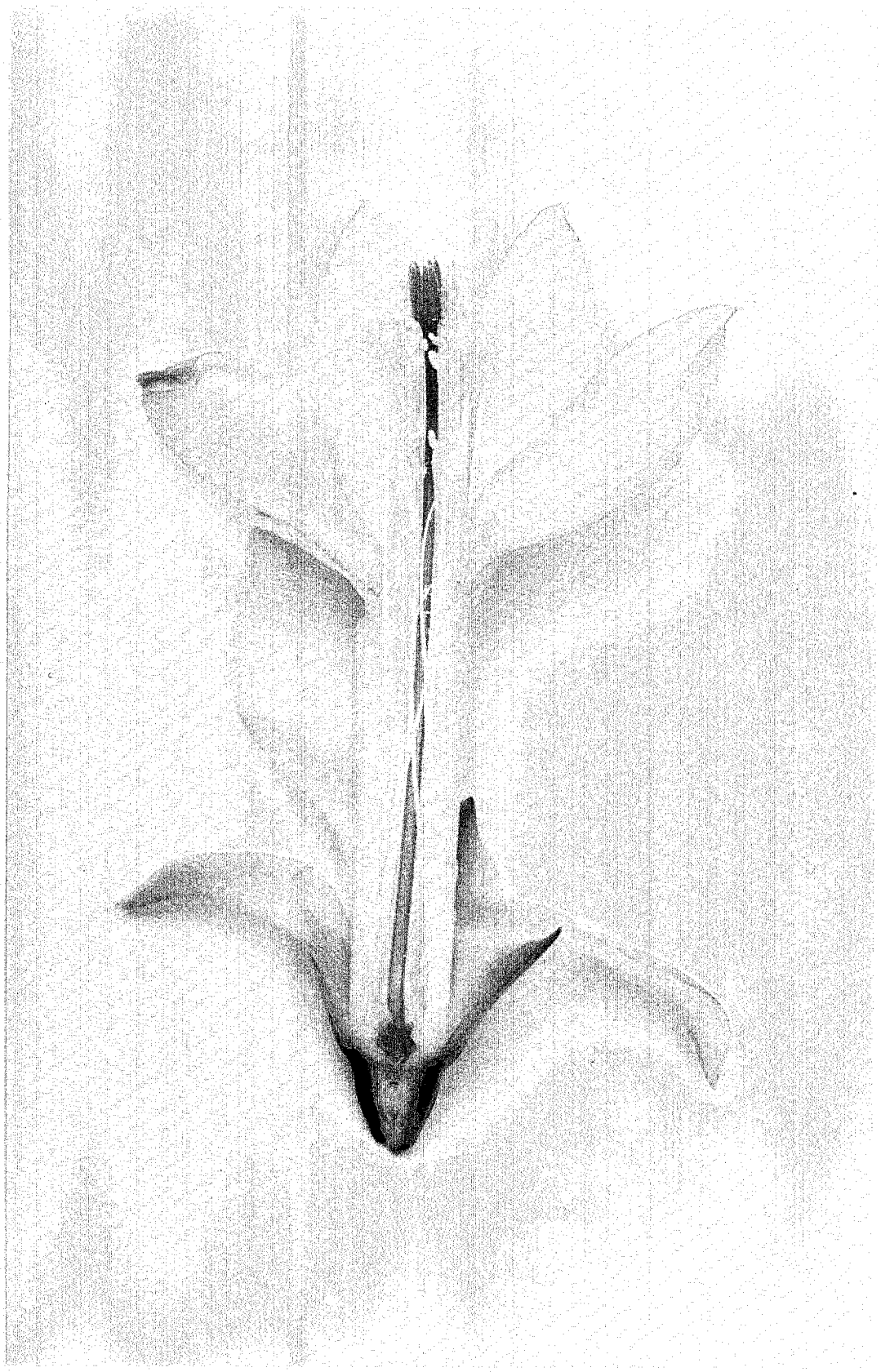

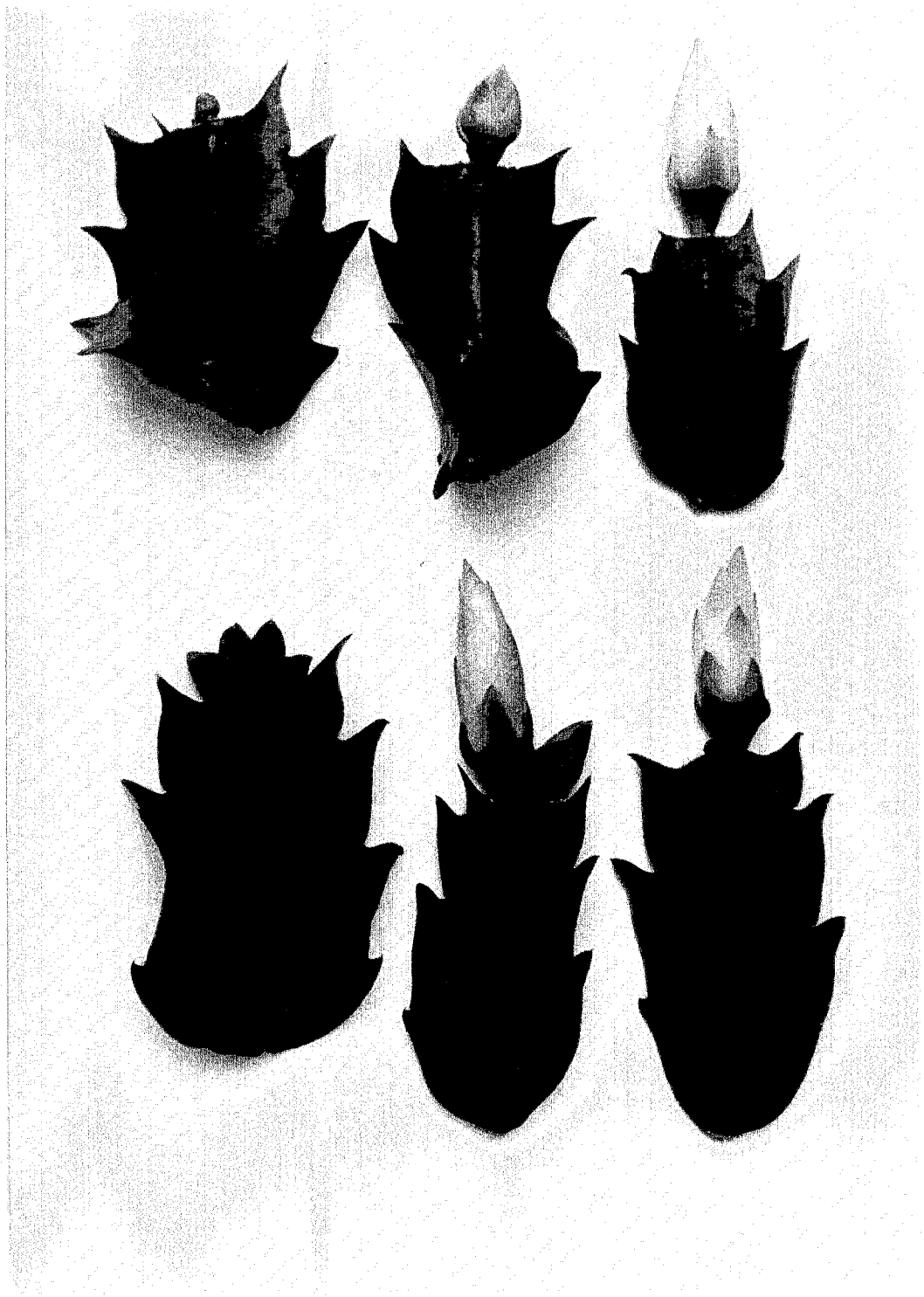

* * * * *